(12) United States Patent
Renner et al.

(10) Patent No.: US 7,896,800 B2
(45) Date of Patent: Mar. 1, 2011

(54) ENDOSCOPE FOR MEDICAL AND NON-MEDICAL PURPOSES

(75) Inventors: Klaus Renner, Emmingen-Liptingen (DE); Werner Schuele, Leibertingen (DE)

(73) Assignee: Karl Storz GmbH & Co. KG (DE)

( * ) Notice: Subject to any disclaimer, the term of this patent is extended or adjusted under 35 U.S.C. 154(b) by 695 days.

(21) Appl. No.: 11/140,335

(22) Filed: May 27, 2005

(65) Prior Publication Data

US 2006/0069308 A1    Mar. 30, 2006

Related U.S. Application Data

(63) Continuation of application No. PCT/EP2004/010643, filed on Sep. 22, 2004.

(30) Foreign Application Priority Data

Sep. 24, 2003    (DE) .................................. 103 44 109

(51) Int. Cl.
*A61B 1/00* (2006.01)
(52) U.S. Cl. ......................................... 600/133; 600/169
(58) Field of Classification Search .................. 600/133, 600/152, 169; 128/898; 606/1
See application file for complete search history.

(56) References Cited

U.S. PATENT DOCUMENTS

| | | | | |
|---|---|---|---|---|
| 2,885,746 A * | 5/1959 | Gura | ............................. | 52/172 |
| 3,965,849 A * | 6/1976 | Gee | ............................. | 116/218 |
| 4,174,225 A * | 11/1979 | Lundgren et al. | ............. | 106/38.6 |
| 4,341,539 A * | 7/1982 | Gidaspow et al. | ............... | 96/127 |
| 4,542,115 A | 9/1985 | Strack et al. | | |
| 4,779,613 A * | 10/1988 | Hashiguchi et al. | .......... | 600/169 |
| 5,060,663 A * | 10/1991 | Rainer | ............................ | 131/777 |
| 5,306,327 A * | 4/1994 | Dingeman et al. | .............. | 75/313 |
| 5,551,671 A * | 9/1996 | McKenzie | ........................ | 266/156 |
| 5,638,834 A * | 6/1997 | White et al. | ..................... | 131/291 |
| 5,657,621 A * | 8/1997 | Mendes et al. | ............. | 56/16.4 D |
| 5,810,620 A * | 9/1998 | Kobayashi et al. | ............ | 439/610 |
| 6,547,722 B1* | 4/2003 | Higuma et al. | ................ | 600/133 |
| 7,011,626 B2* | 3/2006 | Huber et al. | ..................... | 600/133 |
| 2002/0003324 A1* | 1/2002 | Kamikawa et al. | ........... | 266/171 |
| 2002/0155143 A1* | 10/2002 | Campbell et al. | .............. | 424/410 |
| 2004/0127768 A1* | 7/2004 | Huber et al. | ................... | 600/162 |

(Continued)

FOREIGN PATENT DOCUMENTS

DE    195 07 205 A1    11/1995

(Continued)

OTHER PUBLICATIONS

International Search Report; Dec. 7, 2004.

(Continued)

*Primary Examiner* — John P Leubecker
*Assistant Examiner* — Victoria W Chen
(74) *Attorney, Agent, or Firm* — St. Onge Steward Johnston & Reens LLC

(57) ABSTRACT

The invention relates to an endoscope for medical and non-medical purposes having a housing and a shaping element positioned in the housing containing a hygroscopic substance. To design a medical instrument of the aforementioned type in such a manner than the hygroscopic substance can be integrated into the housing simply and securely with the greatest possible drying effect, it is proposed in keeping with the invention that the binding agent is also a hygroscopically active substance.

18 Claims, 2 Drawing Sheets

U.S. PATENT DOCUMENTS

| | | |
|---|---|---|
| 2004/0133069 A1 * | 7/2004 | Shapland et al. ............... 600/37 |
| 2007/0028769 A1 * | 2/2007 | Eplee et al. .................... 95/113 |

FOREIGN PATENT DOCUMENTS

| | | |
|---|---|---|
| DE | 196 47 851 A1 | 2/1998 |
| DE | 101 13 365 A 1 | 10/2002 |
| DE | 203 11 049 U1 | 9/2003 |
| JP | 53096985 A | 8/1978 |
| JP | 58036918 A | 3/1983 |
| JP | 63116727 A | 5/1988 |
| JP | 8022366 B | 3/1996 |
| JP | 2756504 B2 | 5/1998 |
| JP | 101 707 94 A | 6/1998 |
| JP | 2000102508 A | 4/2000 |
| JP | 2000515785 T | 11/2000 |
| JP | 2001053989 A | 2/2001 |
| JP | 3285217 B2 | 5/2002 |
| WO | 9804947 A1 | 2/1998 |
| WO | 02074159 A1 | 9/2002 |
| WO | 020745159 A1 | 9/2002 |

OTHER PUBLICATIONS

English translation of Japanese Office Action, Patent Application No. 2005-518264, Feb. 16, 2009, 5 pages.

English translation of Japanese Office Action, Patent Application No. 2005-518264, Jul. 11, 2008, 14 pages.

\* cited by examiner

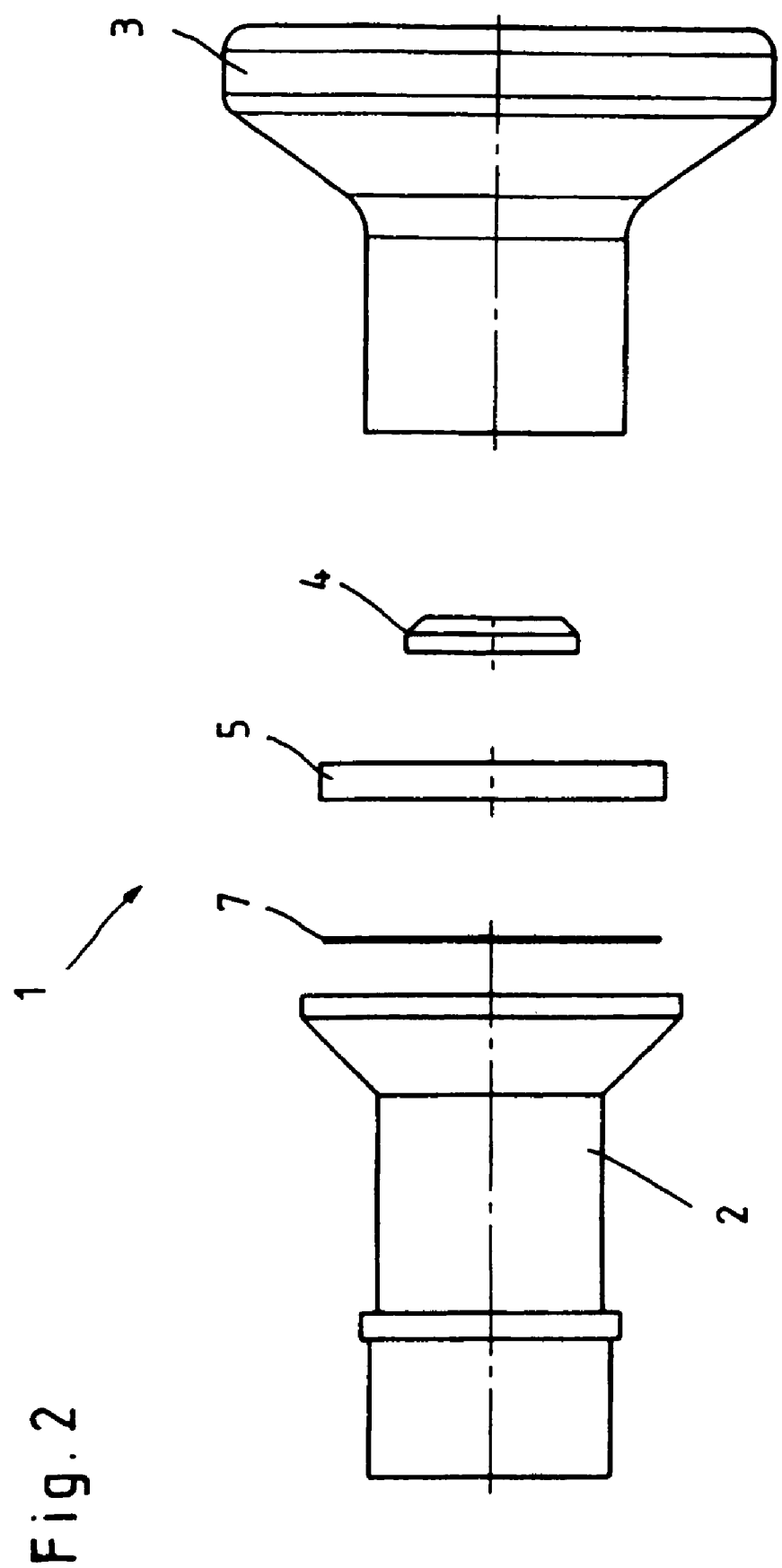

ENDOSCOPE FOR MEDICAL AND NON-MEDICAL PURPOSES

CROSS REFERENCE TO RELATED APPLICATION

This application is a continuation application of co-pending International Patent Application PCT/EP2004/010643 filed on Sep. 22, 2004 which designates the United States and claims priority of German patent application number 103 44 109.3 filed on Sep. 24, 2003 and being fully incorporated by reference herewith.

FIELD OF THE INVENTION

The invention relates to an endoscope for medical and non-medical purposes, having a housing and a shaping element which is positioned in the housing and contains a hygroscopic substance. The invention also relates to a drying agent attachment for this medical instrument.

BACKGROUND OF THE INVENTION

Optical instruments, particularly endoscopes, for medical and non-medical purposes are mainly fluid-tight systems. It remains possible, however, for a series of reasons, that moisture can penetrate the housing, which can lead to a clouding of the optical systems that adversely affects visibility. Problems can occur, for instance, as early as the manufacturing of the instruments in normal atmosphere, if the residual moisture in the atmospheric air is precipitated in the housing interior. In addition, moisture can penetrate because of minor leakiness at joints or seams at which the instrument can be disassembled for purposes of maintenance, repair, or installation. The instruments can suffer additional impacts, for instance with medical endoscopes, from cleaning by means of autoclaving, in which the instrument is exposed to superheated steam at about 140 degrees C. under varying pressure. This temperature impact can result in fine cracks, through which moisture, in turn, can penetrate into the housing.

To avoid such condensation problems from moisture precipitated on the optical system, a familiar method with optical instruments calls for positioning in the housing a hygroscopic substance which binds the moisture occurring inside the housing before it precipitates on the at least one optical system.

Thus, for instance, it is a familiar process to distribute the hygroscopic substance in loose form in the housing. This has the disadvantage, however, that moving the instrument causes noises as well as wearing of the hygroscopic substance, which can settle on the optical systems in the form of dust.

Patent DE 101 13 365 A1 describes an optical instrument. In this instrument the hygroscopic substance is embedded in a shapable matrix material, which can be replaceably inserted into the eyepiece recesses of the instrument. The shapable matrix material thus serves as a support scaffold for the hygroscopic material.

In addition, in DE 195 07 205 A1 it is proposed that the hygroscopic substance should be positioned under a removable wall piece of the housing, which is connected gas-tight with the other housing wall by means of a coupling. This embodiment allows for a rapid, easy replacement of the hygroscopic substance, but with the disadvantage that the endoscope has an additional opening whose fluid-tight quality must be ensured.

SUMMARY OF THE INVENTION

Consequently, it is the object of the invention to provide an endoscope of the aforementioned type in such a way that the hygroscopic substance can be integrated simply and securely into the housing with the greatest possible drying effect. An additional object of the invention is to provide a drying agent arrangement to be positioned in a medical instrument of this type.

The fulfillment of this object according to the invention is characterized in that the connecting material is a hygroscopically effective substance.

Through the invention's use of a hygroscopically active substance as connecting material for producing the shaping element shaped from the drying agent and the binding material, the hygroscopic effect of the actual drying agent is clearly reinforced. The shaping element configured in this way is thus distinguished in that the drying effect it causes is produced not only by the actual hygroscopic substance (for instance, silica gel), but in addition by the connecting agent used for binding and shaping the hygroscopic substance.

According to a practical embodiment of the invention, it is proposed that the hygroscopically active binding agent is an earthenware material and in particular a dry earthenware. For example, the use of bentonite as binding material reinforces the hygroscopic action of the shaping element formed by the hygroscopic substance and the bentonite, because as a soakable multi-layer silicate has the capacity to absorb large quantities of water.

Owing to the inventive configuration of the shaping element exclusively from the hygroscopic substance replaced with a binding material, the amount of the hygroscopic substance for configuring the shaping element can be increased because no matrix material is used as support scaffold, which in turn improves the drying effect.

According to a preferred embodiment of the invention, it is proposed that the mixing proportion of the hygroscopic substance to the binding material in the output mixture, that is before any possible chemical reaction of the two components with one another, is preferably about 4 to 1.

To position the shaping element formed from the hygroscopic substance inside the instrument housing, a recess, for instance in the shape of a groove, is configured in the housing so that there is no loss of construction space in the configuration of the instrument that could adversely affect the other characteristics of the medical instrument.

According to a practical embodiment of the invention, the shaping element is ring-shaped and the related recess in the housing is in the form of a circular groove.

Also proposed with the invention is a drying agent arrangement for positioning in an endoscope. To ensure that absolutely no particle of the shaping element reaches the interior of the instrument, this drying agent arrangement, in addition to the shaping element consisting of the hygroscopic substance combined with a binding agent, includes a sieve that works with the shaping element.

For the configuration of the water-tight permeable sieve, it is proposed that the sieve be configured as fine-meshed, preferably of metal construction or as a permeable membrane.

In a first embodiment of the drying agent arrangement, the sieve is positioned as a separate component on the side of the shaping element facing the inside of the housing. Alternatively, it is further proposed with the invention that the sieve is embedded in the material of the shaping element on the side of the shaping element facing the inside of the housing, so that the shaping element and the sieve, forming a frame, are advantageously encased with a synthetic material, in particular a duroplast.

It is finally proposed with the invention that the hygroscopically active substances forming the shaping element, after assembly and before the first use of the endoscope, can be activated by a corresponding temperature treatment in order to minimize the moisture content of the drying agent and thus to increase its drying capability.

Additional characteristics and advantages of the invention are apparent from the following description of the illustration, in which an embodiment of an inventive endoscope is depicted merely schematically

BRIEF DESCRIPTION OF THE DRAWINGS

FIG. 1b shows an enlarged depiction of the detail from FIG. 1a.

FIG. 2 shows an exploded drawing of the instrument part seen in FIG. 1a. In the part of an instrument shown in FIGS. 1a, 1b, and 2 we see an eyepiece unit 1 of an endoscope, where such an endoscope can be used both for medical and non-medical purposes, for instance technical purposes.

DETAILED DESCRIPTION OF THE DRAWINGS

Figure 1A:
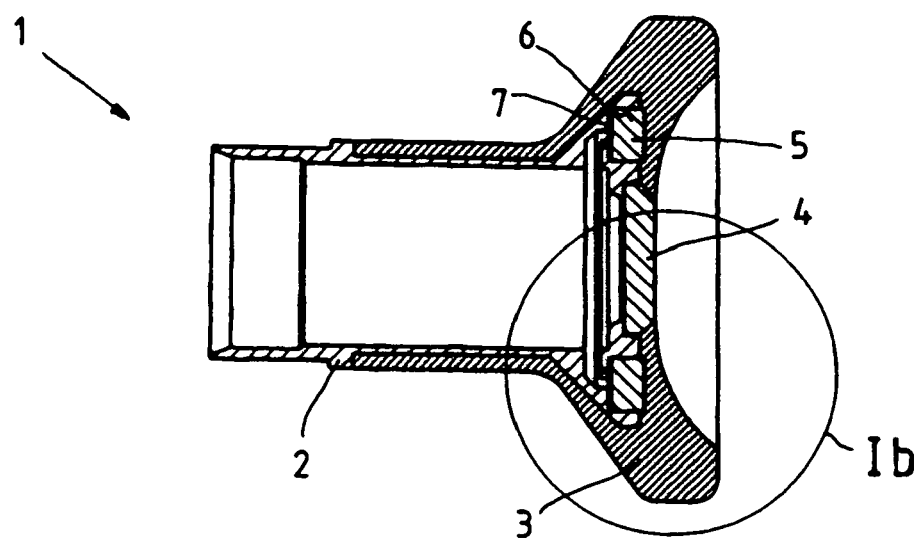
FIG. 1a shows a longitudinal section through a part of an inventive endoscope.
Figure 1B:
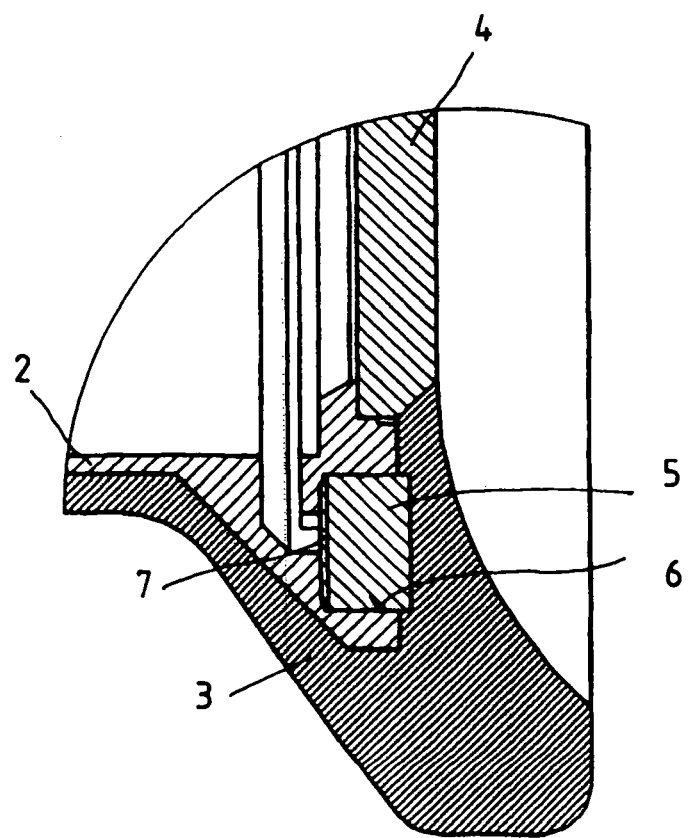

The illustrated eyepiece unit 1 consists essentially of a housing 2, an eyepiece recess 3 positioned on the proximal end of the housing 2, and an eyepiece covering lens 4, which for instance is cemented into the eyepiece recess and closes the eyepiece unit 1 on the proximal side so that it is fluid-tight. On the distal side the eyepiece unit 1 is screwed together with the housing of the not illustrated endoscope, where with the completely installed endoscope at least one optical system is positioned in the inside of the eyepiece unit 1.

To remove residual dampness possibly existing in the housing 2, and to receive moisture penetrating into the housing 2 from leaks, in the inside of the housing 2 a hygroscopic substance such as molecular sieves, for instance synthetic zeolite or other dry earthenware, or else silica gel, is positioned. In particular, the use of, for instance, the one molecular sieve having a pore diameter of 0.4 nm is advantageous as a hygroscopic substance because it can be regenerated at temperatures between 250 and 300 degrees C.

At sufficiently low pressure, very good activation of the drying agent, that is a reduction of the moisture content to below 1%, becomes possible even at a temperature of about 200 degrees C. Total activation of the drying agent, that is a reduction of the moisture content to 0%, generally requires a temperature of about 570 degrees C.

To obtain, on the one hand, the greatest possible drying effect by means of the hygroscopic substance, and, on the other hand, to prevent motion of the instrument from causing wearing of the hygroscopic substance that can be precipitated as dust in the inside of the housing and especially on the optic systems, the hygroscopic substance is replaced with a binding agent and configured as a shaping element 5 that can be inserted in the housing 2. As a binding agent to secure the hygroscopic substance and to make it shapable, it is possible, for instance, to use bentonite or another equally hygroscopically active substance, provided the mixture ratio of the hygroscopic substance to the binding agent in the output mixture, that is before any possible chemical reaction among the components, is preferably about 4:1.

A first pre-activation of the hygroscopically active substances forming the shaping element occurs advantageously just after the assembly and before the first use of the endoscope, in order to minimize the moisture content of the drying agent and thus to increase its drying capacity.

In the embodiment shown in the illustrations, the shaping element 5 is configured as a ring that can be inserted into a surrounding ring-shaped groove 6 in the housing 2. Positioning the shaping element 5 in the ring groove 6 has the advantage that the placement of the drying agent causes no loss of construction space because the ring groove 6 configured in the housing 2 does not reduce the free diameter of the inside of the housing.

In addition to this design of the shaping element 5 as a ring, other configurations, such as spherical shape, are of course possible. In this configuration the spherical shaping elements 5 are to be placed in a cage for stable positioning.

As can further be seen from the illustrations, the drying agent arrangement in the depicted embodiment also includes a water vapor permeable sieve 7, intended to prevent particles of the shaping element 5 from entering the inside of the housing 2. In the illustrated embodiment the sieve 7 is configured as a separate component positioned on the side of the shaping element 5 facing the inside of the housing. Alternatively to this configuration, it is possible to embed the sieve 7 in the material of the shaping element 5 on the side of the shaping element 5 facing the inside of the housing and thus to form a drying agent unit.

The sieve 7 can be configured, for instance, as a fine-mesh sieve preferably of metal construction or as a permeable membrane.

To be able to insert the drying agent arrangement made up of the shaping element 5 and sieve 7 simply and for safe operation in the corresponding recess in the housing 2, the shaping element 5 and the sieve 7, forming a frame with a synthetic material, in particular a duroplast, are sprayed on all sides or otherwise encased, for instance coated, cast, or re-formed.

By producing the shaping element 5 that can be inserted in the housing 2 without a bearing matrix structure exclusively from the hygroscopic substance and the binding agent, the shaping element 5 consists predominantly of the hygroscopic substance so that the greatest possible amount of the hygroscopic substance is available for drying purposes.

In addition, the arrangement is characterized in that such a drying agent arrangement can be simply and rapidly inserted and removed for installation and maintenance purposes.

What is claimed is:

1. An endoscope, having a housing and a single shaping element positioned in the housing and containing a hygroscopic substance, where the shaping element consists exclusively of the hygroscopic substance combined with a binding agent, and wherein the shaping element is configured free of any bearing matrix as a one piece shaping element received on its distal side in a groove in the housing and is retained on its proximal side by an eyepiece recess and wherein the binding agent is also a hygroscopically active substance.

2. An endoscope according to claim 1, characterized in that the binding agent is a dry earthenware material.

3. An endoscope according to claim 2, characterized in that the binding agent is bentonite.

4. An endoscope according to claim 1, characterized in that the shaping element is configured as ring-shaped and the groove in the housing is configured as a ring-shaped groove.

5. An endoscope according to claim 1, comprising a water vapor permeable sieve that works with the shaping element.

6. An endoscope according to claim 5, characterized in that the sieve is configured as a fine-mesh metallic sieve.

7. An endoscope according to claim 5, characterized in that the sieve is positioned on the side of the shaping element facing the inside of the housing.

8. An endoscope according to claim 7, characterized in that the sieve on the side of the shaping element facing the inside of the housing is embedded in the shaping element.

9. An endoscope according to claim 5, characterized in that the shaping element and the sieve, forming a frame, are encased with a synthetic material.

10. An endoscope according to claim 5, characterized in that the hygroscopically active substances forming the shaping element can be activated after the assembly of the endoscope by a corresponding temperature treatment.

11. An endoscope, having a housing and a single shaping element positioned in the housing and containing a hygroscopic substance, where the shaping element consists exclusively of the hygroscopic substance combined with a binding agent, and wherein the shaping element is configured free of any bearing matrix as a one piece shaping element received on its distal side in a groove in the housing and is retained on its proximal side by an eyepiece recess and wherein the binding agent is also a hygroscopically active substance, wherein said endoscope is characterized in that the binding agent is a dry earthenware material; and the mixture ratio of the hygroscopic substance to the binding agent mixture is approximately 4:1.

12. An endoscope of claim 11, wherein the shaping element is configured as ring-shaped and the groove in the housing is configured as a ring-shaped groove.

13. An endoscope according to claim 11, comprising a water vapor permeable sieve that works with the shaping element.

14. An endoscope according to claim 13, characterized in that the sieve is configured as a fine-mesh metallic sieve.

15. An endoscope according to claim 13, characterized in that the sieve is positioned on the side of the shaping element facing the inside of the housing.

16. An endoscope according to claim 15, characterized in that the sieve on the side of the shaping element facing the inside of the housing is embedded in the shaping element.

17. An endoscope according to claim 13, characterized in that the shaping element and the sieve, forming a frame, are encased with a synthetic material.

18. An endoscope according to claim 13, characterized in that the hygroscopically active substances forming the shaping element can be activated after the assembly of the endoscope by a corresponding temperature treatment.

* * * * *